United States Patent [19]

Nosanchuk

[11] Patent Number: 4,875,583
[45] Date of Patent: Oct. 24, 1989

[54] NEEDLE CAP REPLACEMENT DEVICE

[76] Inventor: Jerry L. Nosanchuk, 31130 Sunset, Franklin, Mich. 48025

[21] Appl. No.: 202,396

[22] Filed: Jun. 6, 1988

[51] Int. Cl.⁴ ............................................. B65D 83/10
[52] U.S. Cl. .................................... 206/365; 206/563; 220/1.T
[58] Field of Search .............. 206/365, 438, 562, 563, 206/379, 383, 366, 567; 220/1 T

[56] References Cited

U.S. PATENT DOCUMENTS 4,658,957 4/1987 Guth et al. ........................ 206/365

Primary Examiner—Allen M. Ostrager
Attorney, Agent, or Firm—Gifford, Groh, Sheridan, Sprinkle and Dolgorukov

[57] ABSTRACT

A needle cap replacement device for the purpose of removing, holding and replacing a protective needle cover or cap during the performance of a medical procedure involving a needle and syringe. The needle cap replacement device comprises a block of suitable material having at least one recess wherein the recess has a diameter and a depth for receipt and retention of the needle cap; an elongated cap covering the needle and releasably attached to the distal portion of a syringe. The needle cap replacement device may have more than one recess for the receipt and retention of several needle caps and the recesses may be of varying diameters to accommodate caps of varying sizes. The device may have a disposal chamber for the syringe and needle. Attached to the replacement device at the exterior of the disposal chamber is a receptacle to receive the used needles and syringes.

8 Claims, 1 Drawing Sheet

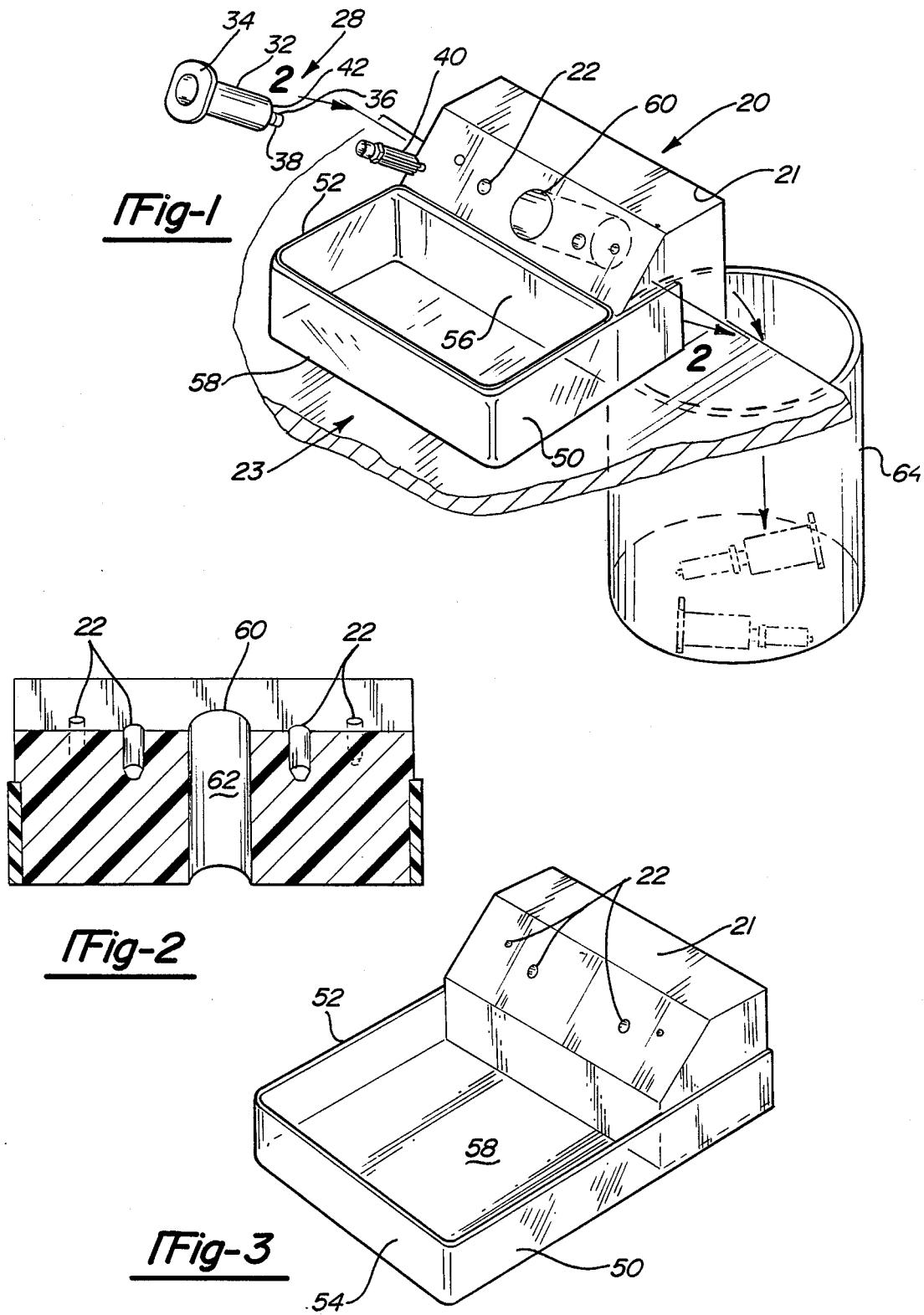

NEEDLE CAP REPLACEMENT DEVICE

BACKGROUND OF THE INVENTION

1. Field of the Invention

This invention concerns a needle cap replacement device for use during a medical procedure involving various types of syringes and attached needles which are protected by caps.

2. Prior Art

The prior art teaches a variety of storage racks, storage trays and organizational devices which facilitate neat, convenient storage and holding containers for test tubes and various medical equipment. The prior art addressed the need for organization of medical equipment, and means for providing convenient access to the equipment during a medical procedure. The prior art does not address a safety device, such as the present invention of the needle cap replacement device, which protects medical personnel from contact and puncture with a contaminated needle during a medical procedure. The present invention is particularly directed towards protecting medical personal and medical care givers from coming into contact with needles contaminated with the AIDS virus.

An example of the prior art referred to is found in U.S. Pat. No. 4,420,085 to Wilson. The Wilson patent describes an organizer for a medical procedure comprising a tray with various compartments to receive assorted sized syringes and vials in a lay-flat or upright condition, providing access to the instrument container during medical procedures.

U.S. Pat. No. 2,790,547 to Sutton teaches a laboratory tray for a medical technician. The tray is designed to make fresh equipment and materials readily accessible during medical procedures and to store used equipment and material. The tray compartments are dimensioned to receive syringes of varying sizes. The tray is designed to hold all equipment and supplies needed by the medical technician to be used in various procedures and provides means of carrying medical equipment and supplies.

U.S. Pat. No. 3,643,812, granted to Mander et al teaches a tube storage rack. The rack is designed to hold a plurality of culture tubes or similar tubular articles in an upright position. The rack is designed to accommodate tubes of varying diameter and length.

The prior art does not anticipate the needle cap replacement device which grips a needle cap, freeing it from its position covering the needle, retains the cap during the medical procedure, facilitates replacement of the cap over the needle and provides a means of disposal for the used syringe and needle.

SUMMARY OF THE INVENTION

The present invention defines a needle cap replacement device for use with a syringe of the type comprising:

a syringe with a hollow barrel wherein the needle is attached to the distal portion of the barrel; and an elongated cap covering the needle and releasably attached to the distal portion of the barrel, the replacement device comprising:

a block of metal or weighted plastic or other weighted material, having at least one hole formed therein, wherein the hole has a diameter and depth for receipt and retention of a needle cap. The block is molded into a plastic, stackable tray. The tray is, preferably a generally rectangular, open top receptacle, having two side walls, a front and rear wall and a full or partial bottom panel.

The needle cap replacement device of the present invention facilitates safe replacement of the cap on the needle after its use in the medical procedure and allows convenient and accessible means of immediate disposal of the contaminated needle. The invention protects medical personal from possible contact with contaminated needles, by accidental skin puncturing themselves therewithin in attempting to replace the needle cap. This protection is increasingly necessary as medical personnel are faced with the ever present risk of accidental contact with various infective agents contained in body fluid.

For a more complete understanding of the present invention reference is made to the following detailed description and accompanying drawing. In the drawing like referenced characters refer to like parts throughout the several means in which:

BRIEF DESCRIPTION OF THE DRAWING

FIG. 1 is a perspective view of the needle cap replacement device;

FIG. 2 is a sectional view of the needle cap replacement device showing the hole for receiving the needle cap and the disposal chamber for the used syringes and needles;

FIG. 3 is an alternative embodiment of the device.

DETAILED DESCRIPTION OF THE PREFERRED EMBODIMENTS

Referring now to FIGS. 1–3 there is shown a needle cap replacement device generally designated 20 comprising a block or stand 21 of suitable weighted plastic, metal or other suitable material having at least one hole or recess 22 to receive at least one needle cap 40, which covers a needle attached to syringe 28. The syringe 28 may be of the type having an elongated hollow barrel 32, a plunger 34 slidably received in the barrel 32, a tip 36 extending distally from the barrel 32 and a hub 38 attached to the tip 36 with the hub 38 having an elongated distally extending needle. As shown, an elongated hollow cap 40 is releasably attached to the hub 38 at a distal portion 42 of the syringe 28 in order to receive and cover the syringe needle.

Any other type of syringe may be used with the apparatus hereof, for example a syringe 42 having a hub attached to its tip, with the hub having an elongated distally extending needle, i.e., the type often used for drawing blood from a patient.

The recess 22 which receives the needle cap is fractionally larger than the diameter of the needle cap to be retained. As shown, the needle cap replacement device may contain a plurality of recesses of varying sizes for the receipt and retention of needle caps of varying sizes.

The block 21 is, preferably, molded as an open bottomed block and into an open top stackable tray or receptacle 23 to enable nestable stacking. The tray comprises two side panels 50, 52, a front panel 54, and rear panel 56 and a bottom panel 58. The tray comprises a lightweight material such as plastic and is easily nested to facilitate stacking. The tray or receptacle may contain various organizer compartments, for holding medical supplies.

In another embodiment of the present device and as shown in FIGS. 1 and 2, there is located in the block 21, a single hole or opening 60 of a diameter larger than that of a syringe, particularly a large syringe for the withdrawal of blood. The hole is formed through to the interior of the block 21, forming a disposal chamber 62 for both the syringe and needle. In this embodiment, the block is formed as a substantially solid mass. A device of this design may be mounted in an open top receptacle having two side panels, a front panel and a partial bottom panel, as hereinbefore. Likewise, it is possible that a waste container or the like 64 be attached to the needle cap replacement device, by any suitable means, for receipt of the used syringe and needle when inserted into the disposal chamber. In such a construction the waste container comprises a material impervious to puncture and leakage.

Ordinarily, though, the block is dimensioned such that a used syringe may be collected in the tray or may be positioned such that the spent syringe may be discarded into the chamber and otherwise disposed of in a suitable container separate and apart from the block and/or tray.

The needle cap replacement device, when properly used protects the person performing a medical procedure from accidental contact and contamination with a used needle and syringe. The needle cap replacement device is used in the following manner. The person administering the medical procedure removes the syringe from the tray, inserts the attached cap in the appropriate sized hole before the medical procedure leaving the needle protecting cap retained within the block. The user then performs the appropriate medical procedure using the syringe and needle, thereafter withdrawing the syringe from the body. Using one hand and protecting the other hand, the user immediately replaces the syringe and used needle in the needle cap mounted within the needle cap replacement device, the needle cap being held in place in the hole 22 by the emplacement thereof. The needle and syringe are secured within the cap mounted therewithin. When the needle "clicks" into the cap securement is achieved. The syringe and capped needle are then withdrawn from the device and disposed of properly. If the needle does not "click" in, the cap can be manually urged onto the needle after the needle end is enshrouded. When using the model containing a disposal chamber, the used needle and syringe are simply dropped into the disposal chamber and received in the attached container. As shown in FIG. 2 the disposal chamber is an optional feature on the needle cap replacement device.

The needle cap replacement device provides convenient, safe and sanitary disposal of needles and syringes, while protecting medical personal from possible contact and/or puncture with contaminated needles and possible infection as a result of such contact. This is particularly important since today's medical personnel constantly face the possibility of contacting various infective agents, which could easily result from accidental contact with a contaminated needle.

The invention accommodates various sized needle caps, retaining them during medical procedures and allowing them to be easily replaced over the needle after the procedure. The disposal chamber facilitates immediate, convenient disposal of the contaminated needle and syringe. Thus, the possibility of inadvertent contact and/or skin puncture is greatly reduced and/or eliminated.

The device is affordable, convenient and easily accessible for use during a medical procedure.

It should, also, be noted with respect hereto that the invention hereof, may be defined by solely, the block 20. In such circumstances the block is molded as an open-bottomed device having a pair of side walls, a top wall, an inclined front wall and a linear or planar rear wall, as shown. In such circumstances, the block is molded to be dimensioned to removably seat within a pre-existing medical tray to be mounted on a wall; to be manually transported or the like.

The foregoing detailed description is given for clearness of understanding only, and no unnecessary limitations should be understood therefrom, as modification will be obvious to those skilled in the art.

What is claimed:

1. A needle cap replacement device for use during a medical procedure comprising:
   a block having a top surface and a bottom surface, a back surface, opposed side surfaces, at least one frontal surface, having at least one rounded recess, wherein the recess has a diameter and a depth for receipt and retention of a needle cap,
   wherein at least one hole having a diameter large enough to receive a syringe and needle, is formed through to the exterior of the block, forming a disposal chamber for the syringe and needle.

2. The needle cap replacement device of claim 1 wherein the recess diameter is cut fractionally larger than the diameter of the needle cap to be retained.

3. The needle cap replacement device of claim 2 wherein the recess secures a needle cap within the hole.

4. The device of claim 3 wherein the block has a plurality of recesses wherein the recesses are of varying sizes to retain varying size needle caps.

5. The needle cap replacement device of claim 4 further comprising a molded plastic, stackable tray, for mounting of the block therein, the tray comprising an open top, generally rectangular receptacle having two side walls, a front wall and a back wall, and a full bottom panel.

6. The device of claim 4 further comprising a tray having two side panels, a front panel and a partial bottom panel, wherein the tray is affixed to the bottom surface of the block, leaving the back surface of the block exposed.

7. The device of claim 1 further comprising a receptacle attached to the needle cap replacement device, whereby a syringe inserted into the disposal chamber may be received and securely retained for later destruction.

8. The device of claim 7 wherein the receptacle comprises a material impervious to puncture and leakage.

* * * * *